United States Patent [19]

Neustadt et al.

[11] 4,304,790
[45] Dec. 8, 1981

[54] 2-(ALKYLTHIO, ALKYLSULFINYL OR ALKYLSULFONYL)-4-[2-ANILINOALKYLAMINO)-1-HYDROXYETHYL]PHENOLS AND DERIVATIVES THEREOF

[75] Inventors: Bernard R. Neustadt; Elijah H. Gold, both of West Orange, N.J.

[73] Assignee: Schering Corporation, Kenilworth, N.J.

[21] Appl. No.: 47,667

[22] Filed: Jun. 12, 1979

[51] Int. Cl.$^3$ .................... A61K 31/135; C07C 91/22
[52] U.S. Cl. ..................................... 424/330; 564/365
[58] Field of Search .................... 424/330; 260/570.6; 564/363, 365

[56] References Cited

U.S. PATENT DOCUMENTS 4,154,761  5/1979  Collins et al. ............... 260/570.5 P
4,163,053  7/1979  Neustadt et al. .................... 424/230

FOREIGN PATENT DOCUMENTS 856055  6/1977  Belgium .............................. 424/330

Primary Examiner—Frederick E. Waddell
Attorney, Agent, or Firm—Anita W. Magatti; Barbara L. Renda; Mary S. King

[57] ABSTRACT

2-(Alkylthio, alkylsulfinyl or alkylsulfonyl)-4-[2-(anilinoalkylamino)-1-hydroxyalkyl]phenols and derivatives thereof, particularly useful as agents for the treatment of hypertension, are disclosed herein.

13 Claims, No Drawings

2-(ALKYLTHIO, ALKYLSULFINYL OR ALKYLSULFONYL)-4-[2-ANILINOALK-YLAMINO)-1-HYDROXYETHYL]PHENOLS AND DERIVATIVES THEREOF

The present invention is concerned with 2-(alkylthio, alkylsulfinyl or alkylsulfonyl)-4-[2-(anilinoalkyl-amino)-1-hydroxyethyl]phenols and derivatives thereof. More particularly, this invention is concerned with compounds of the formula

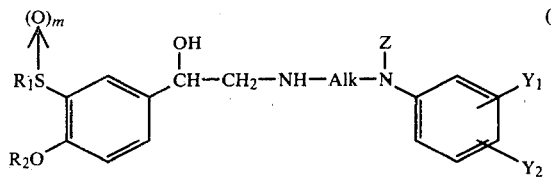

wherein
$R_1$ is lower alkyl;
$R_2$ is hydrogen; aroyl or lower alkanoyl;
m is 0-2;
Alk is an acyclic alkylene bridge containing 2-10 carbon atoms, with the proviso that there are 2-6 adjoining carbon atoms separating the nitrogen atoms;
Z is hydrogen, lower alkyl, lower alkanoyl, aroyl, lower alkylsulfonyl, arylsulfonyl, lower alkoxy (lower-)alkyl or 2,2,2-trifluoroethyl;
$Y_1$ and $Y_2$ are independently hydrogen, halogen, hydroxy, trifluoromethyl, lower alkyl, lower alkoxy, amino, mono or di(lower)alkylamino, lower alkanoylamino, lower alkylsulfonylamino, arylsulfonylamino, N-lower alkyl-N-lower alkanoylamino, or N-lower alkyl-N-lower alkylsulfonylamino; and the pharmaceutically acceptable acid addition salts thereof.

The lower alkyl groups referred to above contain 1-6 carbon atoms and are exemplified by methyl, ethyl, propyl, butyl, pentyl, hexyl and the corresponding branched chain isomers thereof. The lower alkoxy groups likewise contain 1-6 carbon atoms and are typified by methoxy, ethoxy, n-propoxy, isopropoxy, n-butoxy, sec-butoxy, t-butoxy and the like.

The lower alkanoyl groups referred to above contain 1-6 carbon atoms and are typified by formyl, acetyl, butyryl, valeryl and the corresponding branched chain isomers.

The aroyl groups are benzoyl and benzoyl optionally substituted by one or two lower alkyl groups and which contain up to 12 carbon atoms, e.g., o-toluoyl, m-toluoyl, p-toluoyl, 3,4-dimethylbenzoyl, m-isopropylbenzoyl and the like.

The aryl groups referred to above are phenyl and phenyl optionally substituted independently by one or two lower alkyl or halogen groups, e.g., o-tolyl, p-tolyl, 3,4-dimethylphenyl, 4-chlorophenyl and the like.

The halogen atoms represented by $Y_1$ and $Y_2$ include fluorine, chlorine, bromine and iodine.

The Alk bridges containing 2-10 carbon atoms and having 2-6 adjoining carbon atoms separating the nitrogen atoms are represented by acyclic alkylene groups such as ethylene, trimethylene, tetramethylene and pentamethylene groups optionally substituted by lower alkyl groups. Thus, representative Alk groups of this invention are ethylene, 1-methylethylene, trimethylene or propylene, 1-methyltrimethylene, tetramethylene, 1-methyltetramethylene, 1,1-dimethyltrimethylene, 1,2-dimethyltrimethylene, 1-ethyltrimethylene, 1-methyl-2-ethyltetramethylene, pentamethylene, and 1,1-dimethyl-3-methylpentamethylene.

Preferred compounds of this invention are represented by the formula

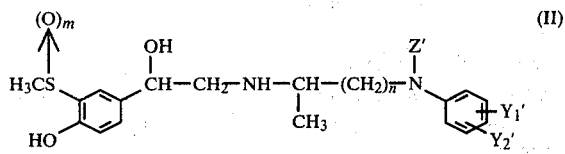

wherein n is 1-4; $Z'$ is hydrogen or lower alkyl; and $Y_1'$ and $Y_2'$ are independently hydrogen, halogen, hydroxy, trifluoromethyl, lower alkyl, lower alkoxy or amino; and m is as hereinbefore defined. Particularly preferred compounds of formula I and II are those wherein n is 2, i.e., the Alk bridge is of the formula

The pharmaceutically acceptable acid addition salts of the compounds of formula I may be derived from a variety of organic and inorganic acids, such as sulfuric, phosphoric, hydrochloric, hydrobromic, sulfamic, citric, lactic, oleic, succinic, tartaric, cinnamic, acetic, benzoic, gluconic, ascorbic and related acids.

Preferred compounds of this invention are:
2-methylthio-4-(2-[4-(N-methylanilino)-2-butylamino]-1-hydroxyethyl)phenol;
2-methylsulfinyl-4-(2-[4-(N-methylanilino)-2-butylamino]-1-hydroxyethyl)phenol;
2-methylthio-4-(2-[4-(N-methyl-4-methoxyanilino)-2-butylamino]-1-hydroxyethyl)phenol;
2-methylsulfinyl-4-(2-[4-(N-methyl-4-methoxyanilino)-2-butylamino]-1-hydroxyethyl)phenol;
2-methylsulfonyl-4-(2-[4-(N-methyl-4-methoxyanilino)-2-butylamino]-1-hydroxyethyl)phenol;
2-methylsulfinyl-4-(2-[4-(4,N-dimethylanilino)-2-butylamino]-1-hydroxyethyl)phenol;
2-methylsulfinyl-4-(2-[4-(4-fluoro-N-methylanilino)-2-butyl-amino]-1-hydroxyethyl)phenol; and
2-methylsulfinyl-4-(2-[5-(N-methylanilino)-2-pentylamino]-1-hydroxyethyl)phenol; and
2-methylsulfinyl-4(2-[5-(4-methoxy-N-methylanilino)-2-pentylamino]-1-hydroxyethyl)phenol.

A method for the preparation of the compounds of formula I involves the reaction of an anilinoalkyl amine of the formula

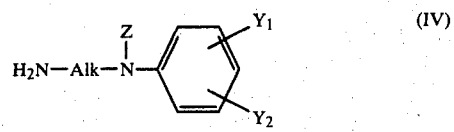

wherein Alk, Z, $Y_1$ and $Y_2$ are as hereinbefore defined, with a compound of the formula

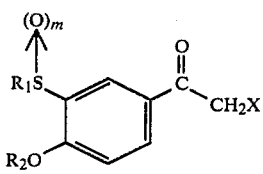

wherein X is chloro or bromo, and $R_1$, $R_2$ and m are as hereinbefore defined, in a suitable solvent in the presence of an acid acceptor to give the compound of the formula

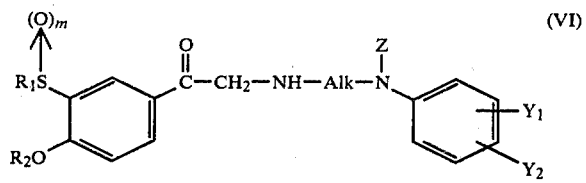

wherein $R_1$, $R_2$, m, Alk, Z, $Y_1$ and $Y_2$ are as hereinbefore defined. The acid acceptor may be an organic base such as pyridine or triethylamine, or an inorganic base such as sodium or potassium carbonate.

In order to obtain compounds of formula VII wherein $R_2$ is hydrogen, it is more convenient to employ in the condensation compounds of formula V wherein $R_2$ is alkanoyl or aroyl. The resulting compounds of formula VII wherein $R_2$ is alkanoyl or aroyl are then converted to compounds of formula VII wherein $R_2$ is hydrogen by hydrolysis, preferably by an aqueous base such as potassium hydroxide.

The resultant compound of formula VI is then reduced to afford the corresponding hydroxy compound of the formula

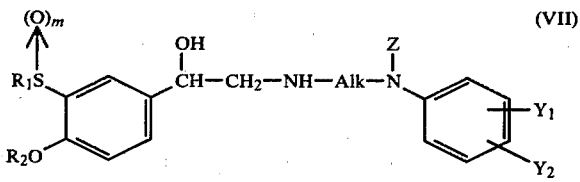

wherein $R_1$, $R_2$, m, Alk, Z, $Y_1$ and $Y_2$ are as hereinbefore defined. A particularly suitable reducing agent for this process is sodium borohydride but other common ketone reducing agents such as lithium borohydride, potassium borohydride and hydrogen may also be utilized.

The compounds of formula I wherein m is 1 or 2 are preparable by oxidation of the corresponding compound of formula I wherein m is 0 with a suitable oxidizing agent such as peracetic acid. The sulfinyl (m=1) compounds are obtained by employing only a slight stoichiometric excess of the peracid, while use of more than two equivalents of the oxidizing agent results in the sulfonyl (m=2) compounds. Alternately this oxidation may be performed at any stage of the synthetic sequence to ultimately afford the desired compounds.

The compounds of formula I wherein the Alk bridge is of the formula

wherein n is 1–4 may be alternately prepared by reaction of a substituted anilinoketone of the formula

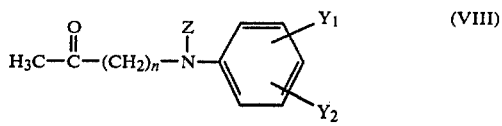

wherein Z, $Y_1$, $Y_2$ and n are as hereinbefore defined, with the appropriate phenol of the formula

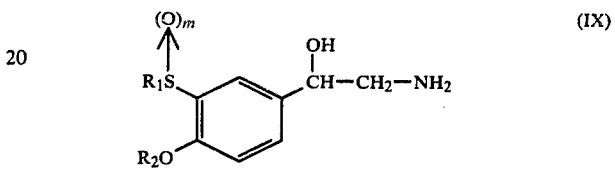

wherein $R_1$, $R_2$, and m are as hereinbefore defined, in the presence of a reducing agent. The reaction is typically conducted in an organic solvent, with lower alkanols such as methanol, ethanol, and 2-propanol being preferred. Sodium cyanoborohydride is a highly preferred reducing agent, but others, such as sodium borohydride and lithium tetrahydrothexyllimonyl borohydride may also be utilized.

The following compounds are representative of the invention:

2-methylthio-4-(2-[4-(N-methylanilino)-2-butylamino]-1-hydroxyethyl)phenol;

2-methylthio-4-(2-[4-(4,N-dimethylanilino)-2-butylamino]-1-hydroxyethyl)phenol;

2-methylthio-4-(2-[4-(4-chloro-N-methylanilino)-2-butylamino]-1-hydroxyethyl)phenol;

2-methylsulfinyl-4-(2-[4-(3-chloro-4-methoxy-N-methylanilino)-2-butylamino]-1-hydroxyethyl)phenol;

2-methylsulfinyl-4-(2-[4-(4-fluoro-N-methylanilino)-2-butylamino]-1-hydroxyethyl)phenol;

2-methylsulfonyl-4-(2-[4-(4-hydroxy-N-methylanilino)-2-butylamino]-1-hydroxyethyl)phenol;

2-methylthio-4-(2-[4-(4-(N-methylmethanesulfonylamino)anilino)-2-butylamino]-1-hydroxyethyl)phenol;

2-methylsulfinyl-4-(2-[4-(4-(N-methylacetylamino)-N-methylanilino)-2-butylamino]-1-hydroxyethyl)phenol;

2-methylsulfonyl-4-(2-[4-(4-amino-N-methylanilino)-2-butylamino]-1-hydroxyethyl)phenol;

2-ethylthio-4-(2-[4-(4-acetamido-N-methylanilino)-2-butylamino]-1-hydroxyethyl)phenol;

2-methylthio-4-(2-[4-(4-methylamino-N-methylanilino)-2-butylamino]-1-hydroxyethyl)phenol;

2-n-propylsulfinyl-4-(2-[4-(4-methanesulfonylamino-N-methylanilino)-2-butylamino]-1-hydroxyethyl)phenol;

2-methylthio-4-(2-[4-(4-trifluoromethyl-N-benzenesulfonylanilino)-2-butylamino]-1-hydroxyethyl)phenol;

2-methylsulfinyl-4-(2-[4-(3-trifluoromethyl-N-benzoylanilino)-2-butylamino]-1-hydroxyethyl)phenol;

2-methylthio-4-(2-[4-(3-methoxy-N-methylanilino)-2-butylamino]-1-hydroxyethyl)phenol;
2-methylsulfinyl-4-(2-[4-(3-hydroxy-N-methylanilino)-2-butylamino]-1-hydroxyethyl)phenol;
2-methylsulfinyl-4-(2-[4-(2,N-dimethylanilino)-2-butylamino]-1-hydroxyethyl)phenol;
2-methylsulfinyl-4-(2-[4-(2-chloro-N-methylanilino)-2-butylamino]-1-hydroxyethyl)phenol;
2-ethylsulfinyl-4-(2-[4-(4-ethoxy-N-methylanilino)-2-butylamino]-1-hydroxyethyl)phenol;
2-n-butylsulfinyl-4-(2-[4-(4-isopropyl-N-methylanilino)-2-butylamino]-1-hydroxyethyl)phenol;
2-methylthio-4-(2-[4-(3-benzenesulfonylamino-N-methylanilino)-2-butylamino]-1-hydroxyethyl)-phenol;
2-methylsulfonyl-4-[2-(4-anilino-2-butylamino)-1-hydroxyethyl]phenol;
2-methylsulfinyl-4-(2-[4-(N-methanesulfonylanilino)-2-butylamino]-1-hydroxyethyl)phenol;
2-methylsulfinyl-4-(2-[4-(N-acetylanilino)-2-butylamino]-1-hydroxyethyl)phenol;
2-methylsulfinyl-4-(2-[4-(N-(2,2,2-trifluoroethyl)anilino)-2-butylamino]-1-hydroxyethyl)phenol;
2-methylsulfinyl-4-(2-[4-(N-ethylanilino)-2-butylamino]-1-hydroxyethyl)phenol;
2-methylsulfinyl-4-(2-[3-(N-methylanilino)-2-propylamino]-1-hydroxyethyl)phenol;
2-methylsulfinyl-4-(2-[3-(N,4-dimethylanilino)-2-propylamino]-1-hydroxyethyl)phenol;
2-methylsulfinyl-4-[2-(3-anilino-2-propylamino)-1-hydroxyethyl]-phenol;
2-methylthio-4-(2-[5-(N-methylanilino)-2-pentylamino]-1-hydroxyethyl)phenol;
2-methylsulfinyl-4-(2-[5-(N-methylanilino)-2-pentylamino]-1-hydroxyethyl)phenol;
2-methylsulfinyl-4-(2-[5-(N,4-dimethylanilino)-2-pentylamino]-1-hydroxyethyl)phenol;
2-methylsulfinyl-4-[2-(5-anilino-2-pentylamino)-1-hydroxyethyl]-phenol;
2-methylsulfinyl-4-(2-[6-(N-methylanilino)-2-hexylamino]-1-hydroxyethyl)phenol;
2-methylsulfinyl-4-(2-[3-(N,4-dimethylanilino)-1-propylamino]-1-hydroxyethyl)phenol;
2-methylsulfinyl-4-[2-(6-anilino-2-hexylamino)-1-hydroxyethyl]-phenol;
2-methylsulfinyl-4-[2-[4-(N-methylanilino)-2-(3-methyl)butylamino]-1-hydroxyethyl)phenol;
2-methylsulfinyl-4-(2-[4-(N-methylanilino)-2-pentylamino]-1-hydroxyethyl)phenol;
2-methylsulfinyl-4-(2-[3-(N-methylanilino)-2-butylamino]-1-hydroxyethyl)phenol;
1-benzoyloxy-2-methylsulfinyl-4-(2-[4-(N-methylanilino)-2-butylamino]-1-hydroxyethyl)benzene; and
1-acetoxy-2-methylsulfinyl-4-(2-[4-(N-methylanilino)-2-butylamino]-1-hydroxyethyl)benzene.

The compounds of this invention are produced by the foregoing methods as stereoisomeric mixtures, i.e., they possess one or more asymmetric carbon and sulfur (wherein m is 1) atoms and therefore exit as chiral mixtures. The compounds may be used as their mixtures or separated into their enantiomeric and diastereomeric pure forms using conventional methods for the separation of such mixtures, such as fractional crystallization and chromatography. In addition, a desired enantiomer may be obtained utilizing pure chiral starting materials.

The compounds of the present invention are useful in the treatment of cardiovascular disorders and particularly in the treatment of mammalian hypertension. Based on laboratory tests, it is considered that the effective dose (ED$_{50}$) by oral administration for a compound of the present invention will typically lie within the range of 0.05 to 10 mg/kg of mammalian weight.

The required daily dosage may be administered in single or divided doses. The exact dose to be administered will, of course, be dependent upon various factors such as the particular compound employed, age and weight of the subject mammal and the individual's response.

The compounds are preferably and most advantageously administered orally. The compounds may be combined with any suitable pharmaceutical carrier and administered in a variety of formulations such as tablets, capsules, syrups, elixirs or suspensions. The compounds may also be administered parenterally.

Typical acceptable pharmaceutical carriers for use in formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate, polyvinylpyrrolidone; polyvinyl alcohol; stearic acid; alkaline earth metal stearates such as magnesium stearate and calcium stearate; stearic acid vegetable oils such as peanut oil, cottonseed oil, sesame oil, olive oil and corn oil; nonionic, cationic and anionic surfactants; ethylene glycol polymers; beta-cyclodextrin; fatty alcohols; and hydrolyzed cereal solids; as well as other non-toxic compatible fillers, binders, disintegrants and lubricants commonly used in pharmaceutical formulations.

In treating certain patients with the compounds of this invention, it may be desirable to include other pharmaceutically active ingredients in the same dosage unit. For example, in treating patients in whom salt and water retention is a problem, effective amounts of conventional diuretics, e.g., hydrochlorothiazide or trichloromethiazide, may be added.

A further aspect of the present invention involves a novel process for the preparation of the intermediate of formula IV wherein the Alk bridge has three adjoining carbon atoms separating the nitrogen atoms. These intermediates are also useful for the preparation of intermediates useful for preparing the antihypertensive agents disclosed and claimed in U.S. Ser. No. 864,983, filed Dec. 27, 1977, now U.S. Pat. No. 4,163,053, entitled "5-[2-(Substituted anilinoalkylamino-1-hydroxyalkyl]salicylamides". More particularly, this novel process is a process for the preparation of the compounds of the formula

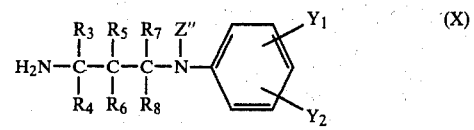

wherein Y$_1$ and Y$_2$ are independently hydrogen, halogen, hydroxy, trifluoromethyl, lower alkyl, lower alkoxy, amino, mono- or di(lower)alkylamino, lower alkanoylamino, lower alkylsulfonylamino, arylsulfonylamino, N-lower alkyl-N-lower alkylsulfonylamino, R$_3$, R$_4$, R$_5$, R$_6$, R$_7$ and R$_8$ are independently hydrogen or alkyl of one to six carbon atoms with the proviso that no more than two of R$_3$, R$_4$, R$_5$, R$_6$, R$_7$ and $R_8$ are alkyl, and $Z''$ is hydrogen, alkyl or lower alkoxy(lower)alkyl; which comprises:

(a) reaction of an N-protected azetidine of the formula:

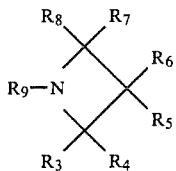   (XI)

wherein $R_9$ is an N-protecting group removable by hydrogenation, and $R_3$, $R_4$, $R_5$, $R_6$, $R_7$ and $R_8$ are as hereinbefore defined, with an aniline of the formula:

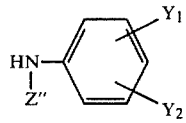   (XII)

wherein $Y_1$, $Y_2$ and $Z''$ are as hereinbefore defined, in the presence of a strong acid, to afford an intermediate of the formula:

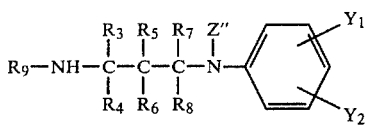   (XIII)

wherein $R_3$, $R_4$, $R_5$, $R_6$, $R_7$, $R_8$, $R_9$, $Z''$, $Y_1$, $Y_2$ are as hereinbefore defined; and (b) removal of the $R_9$ protecting group by hydrogenation.

The reaction step (a) may be conducted in the presence or absence of a solvent, but most preferably an organic solvent is used. Particularly suitable solvents are the alkanols such as ethanol, n-butanol and others such as dimethylformamide and dimethylsulfoxide. Temperature is not critical but reflux generally shortens the length of the reaction time. Typical reaction times vary from 12–48 hours depending upon the solvent, temperature and the particular reactants involved.

The acid may be any strong acid such as a hydrohalic, sulfonic or phosphoric acid. A particularly preferred acid is methanesulfonic, but others such as hydrochloric, hydrobromic, or p-toluenesulfonic may also be used. It is preferable that the quantity of acid used be such that non-protonated aniline of formula XII be available for reaction.

The $R_9$ N-protecting group may be any N-protecting group removable by hydrogenation, such as benzyl, p-methoxybenzyl and benzhydryl and the like, with benzhydryl being most preferred. The hydrogenation is typically conducted at room temperature for ½ to 3 hours using a suitable catalyst. Suitable catalysts are those such as palladium hydroxide on carbon or palladium on charcoal, with 20% palladium hydroxide on carbon being particularly preferred.

The azetidines of formula XI are preparable by methods described in *Tetrahedron Letters*, 44 3921, (1969).

The compounds of formula XIII wherein $Z''$ is hydrogen may be used to prepare, by conventional methods, the corresponding compounds of formula IV wherein Z is lower alkanoyl, aroyl, lower alkylsulfonyl, arylsulfonyl or 2,2,2-trifluoroethyl.

The following examples describe in detail compounds illustrative of the present invention and methods which have been devised for their preparation. It will be apparent to those skilled in the art that many modifications, both of materials and methods, may be practiced without departing from the purpose and intent of this disclosure.

EXAMPLE 1

2-Methylthio-4-(2-[4-(N-Methylanilino)-2-Butylamino]-1-Hydroxyethyl)phenol

A. 4-(N-methylanilino)-2-butanone oxime

Add hydroxylamine hydrochloride (4.9 g=70 mmol) in 20 ml water to a solution of 4-(N-methylanilino)-2-butanone (12.4 g=70 mmol) and sodium carbonate (8.6 g=80 mmol) in 60 ml 50% ethanol. Stir for three days, concentrate and extract with ethyl acetate. Dry, concentrate and recrystallize from ether-hexane to obtain product having a melting point 46°–49° C.

B. 4-(N-methylanilino)-2-butylamine

Combine the oxime prepared in paragraph A (6.3 g=32 mmol) with 50 g Raney nickel and 300 ml ethanol. Hydrogenate at 3 atmospheres pressure for 1 hour, filter, concentrate and distill to obtain 4-(N-methylanilino)-2-butylamine, having a boiling point of 84° C./0.1 mm pressure.

C. 4'-benzoxyloxy-3'-methylthio-2-[4-(N-methylanilino)-2-butylamino]acetophenone hydrobromide Add the amine prepared in paragraph B (3.56 g=20 mmol) to a mixture of 4'-benzoyloxy-3'-methylthio-2-bromoacetophenone (3.56 g=10 mmol) and potassium carbonate (2.76 g=20 mmol) in 40 ml dimethylformamide. After one-half hour, dilute with 70 ml chloroform, then add 8 ml 48% hydrobromic acid. Add 50 ml water and separate the organic layer. Dry and concentrate to obtain the title compound as an oil.

D. 2-methylthio-4-(2-[4-(N-methylanilino)-2-butylamino]-1-hydroxyethyl)phenol

To the aminoketone hydrobromide prepared in paragraph C (5.4 g=10 mmol) in 50 ml methanol, add sodium borohydride (0.4 g=10 mmol) over 1 hour. Stir one-half hour and add 10 ml 10% potassium hydroxide solution. Reflux 1 hour and concentrate. Adjust the pH to about 9 and extract with ethyl acetate. Combine the organic layers, dry, and concentrate to obtain the title product as a brown oil.

EXAMPLE 2

4-(2-[4-(N-methylanilino)-2-butylamino]-1-hydroxyethyl)-2-methylsulfinylphenol hydrochloride To 2-methylthio-4-(2-[4-(methylanilino)-2-butylamino]-1-hydroxyethyl)phenol (1.8 g=5 mmol) in 50 ml methanol add a solution of 40% peracetic acid (5.0 mmol) in 10 ml methanol. Stir one-half hour and concentrate to obtain a gum. Chromatograph on 100 g silica gel using chloroform/methanol/ammonia as eluant and combine appropriate fractions and concentrate to obtain 4-(2-[4-(N-methylanilino)-2-butylamino]-1-hydroxyethyl)-2-methylsulfinylphenol. Dissolve this in ether and treat with ethereal hydrogen chloride to obtain the title product.

EXAMPLE 3

2-methylthio-4-(2-[5-(N-methylanilino)-2-pentylamino]-1-hydroxyethyl)phenol

A. 4'-benzoyloxy-3'-methylthio-2-(trifluoroacetamido)acetophenone

Add trifluoroacetamide (6.8 g=60 mmol) and potassium carbonate (8.0 g=60 mmol) to a solution of 4'-benzoyloxy-3'-methylthio-2-bromoacetophenone (11.0 g=30 mmol) in 200 ml acetonitrile. Reflux for 16 hours, allow to cool, filter, and concentrate. Dissolve the residue in ethyl acetate, wash with 1.0 N sodium hydroxide, then water. Dry, concentrate and treat the residue with ether to obtain the product as a yellow solid.

B. 4-(2-amino-1-hydroxyethyl)-2-(methylthio)phenol

To the amide prepared in paragraph A (8.1 g=20 mmol) in 200 ml ethanol, add sodium borohydride (0.8 g=20 mmol). Stir 1 hour, and add 50 ml 10% potassium hydroxide solution. Reflux 1 hour, allow to cool, and concentrate. Adjust to pH 1 and extract with ethylacetate. Readjust the aqueous layer to pH 8 and extract four times with chloroform. Dry and concentrate the organic layers to obtain the product as a yellow gum.

C. 5-(N-methylanilino)-2-pentanone

Combine 5-chloro-2-pentanone ethylene ketal (80 g=0.49 mol), N-methylaniline (52 g=0.49 mol), potassium carbonate (67 g=0.49 mol) and potassium iodide (8.1 g) in 250 ml dimethylformamide and heat at 100° C. for 16 hours. Allow to cool, partition between ether and water, and wash the ether twice with water. Dry, concentrate and distill to obtain 5-(N-methylanilino)-2-pentanone ethylene ketal, boiling point 104°–109° C./0.1 mm. Dissolve this (47 g=0.20 mol) in 400 ml 1.0 N hydrochloric acid with 100 ml ethanol. Let stand 2 hours, concentrate and adjust pH to about 8. Extract with ethyl ether, dry, concentrate and distill to obtain the product, having a boiling point 100°–104° C./0.1 mm pressure.

D. 2-methylthio-4-(2-[5-(N-methylanilino)-2-pentylamino]-1-hydroxyethyl)phenol

To a solution of the ketone prepared in paragraph C (2.9 g=15 mmol) and 4-(2-amino-1-hydroxyethyl)-2-(methylthio)phenol (prepared in paragraph B) (3.0 g=15 mmol) in 50 ml methanol, add sodium cyanoborohydride (0.9 g=15 mmol). Stir 16 hours, concentrate, dissolve in ethylacetate and wash with sodium carbonate solution. Dry and concentrate to obtain the title compound.

EXAMPLE 4

2-methylsulfinyl-4-(2-[5-(N-methylanilino)-2-pentylamino]-1-hydroxyethyl)phenol hydrochloride To 2-methylthio-4-(2-[5-(N-methylanilino)-2-pentylamino]-1-hydroxyethyl)phenol, (3.7 g=10 mmol) in 100 ml methanol at −5° C., and dropwise a solution of 40% peracetic acid (10 mmol) in 20 ml methanol. Stir one-half hour and concentrate to obtain a gum. Chromatograph on 200 g silica gel using chloroform/methanol/ammonia as eluant, combine fractions and concentrate to obtain 2-methylsulfinyl-4-(2-[5-(N-methylanilino)-2-pentylamino-1-hydroxyethyl)phenol. Dissolve this in ethyl acetate and treat with ethereal hydrogen chloride to give the title product.

EXAMPLE 5

4-(N-methylanilino)-2-butylamine

A. 1-benzhydryl-2-methylazetidine

Combine benzhydrylamine (27.5 g=0.15 ml), 1,3-dibromobutane (40.5 g=0.19 mol) and sodium carbonate (28 g=0.33 mol) in 250 ml acetonitrile. Reflux 24 hours, allow to cool, filter and concentrate. Dissolve the residue in ether and wash with 1% sodium carbonate solution. Dry, concentrate and distill to obtain the product, boiling point 110°–115° C./0.1 mm pressure.

B. N-methyl-N-[3-(benzhydrylamino)butyl]aniline

Combine the above amine (39 g=0.16 mol) and N-methylanilinium methanesulfonate (33 g=0.16 mol) in 500 ml ethanol and reflux for 5 days. Allow to cool, concentrate, dissolve the residue in ethyl acetate and allow to stand. Filter to obtain methanesulfonate salt of the product, melting point 162°–164° C.

C. 4-(N-methylanilino)-2-butylamine

Partition the above amine salt between ethyl acetate and 1.0 N sodium hydroxide. Dry and concentrate the ethyl acetate layer to obtain the free base. Hydrogenate this (34 g=0.10 mol) in 800 ml ethanol with 6.5 g 20% palladium hydroxide/C catalyst for 1 hour. Filter the catalyst and concentrate the filtrate. Partition the concentrated filtrate between ether and 1.0 N hydrochloric acid. Adjust the aqueous layer to pH 14 and extract with ether. Dry and concentrate the ether extracts. Distill to obtain the title product, boiling point 85° C./0.1 mm pressure.

What is claimed is:

1. A compound of the formula

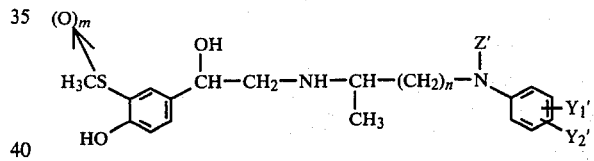

wherein n is 1–4; m is 0–2; Z' is hydrogen or lower alkyl; $Y_1'$ and $Y_2'$ are independently hydrogen, halogen, hydroxy, trifluoromethyl, lower alkyl, lower alkoxy or amino; and the pharmaceutically acceptable acid addition salts thereof.

2. A compound according to claim 1 wherein n is 2.

3. A compound according to claim 1 which is 2-methylsulfinyl-4-(2-[5-(N-methylanilino]-2-pentylamino-1-hydroxyethyl)phenol.

4. A compound according to claim 1 which is 2-methylsulfinyl-4-(2-[5-(4-methoxy-N-methylanilino]-2-pentylamino-1-hydroxyethyl)phenol.

5. A compound according to claim 2 which is 2-methylthio4-(2-[4-N-methylanilino)-2-butylamino]-1-hydroxyethyl)phenol.

6. A compound according to claim 2 which is 2-methylsulfinyl-4-(2-[4-(N-methylanilino)-2-butylamino]-1-hydroxyethyl)phenol.

7. A compound according to claim 2 which is 2-methylthio-4-(2-[4-(N-methyl-4-methoxyanilino)-2-butylamino]-1-hydroxyethyl)phenol.

8. A compound according to claim 2 which is 2-methylsulfinyl-4-(2-[4-(N-methyl-4-methoxyanilino)-2-butylamino]-1-hydroxyethyl)phenol.

9. A compound according to claim 2 which is 2-methylsulfonyl-4-(2-[4-(N-methyl-4-methoxyanilino)-2-butylamino]-1-hydroxyethyl)phenol.

10. A compound according to claim 2 which is 2-methylsulfinyl-4-(2-[4-(4,N-dimethylanilino)-2-butylamino]-1-hydroxyethyl)phenol.

11. A compound according to claim 2 which is 2-methylsulfinyl-4-(2-[4-(4-fluoro-N-methylanilino)-2-butylamino]-1-hydroxyethyl)phenol.

12. A pharmaceutical composition useful in the treatment of hypertension containing an antihypertensive amount of a compound of claim 1 together with a pharmaceutical carrier thereof.

13. A method of reducing hypertension comprising administering to a hypertensive mammal a composition of claim 12 in an amount sufficient to reduce said hypertension.

* * * * *